United States Patent
Kanou et al.

(10) Patent No.: US 8,937,199 B2
(45) Date of Patent: Jan. 20, 2015

(54) STABLE AQUEOUS ACRYLAMIDE SOLUTION

(75) Inventors: Makoto Kanou, Yokohama (JP); Norifumi Hagiya, Yokohama (JP)

(73) Assignee: Mistubishi Rayon Co., Ltd., Tokyo (JP)

( * ) Notice: Subject to any disclaimer, the term of this patent is extended or adjusted under 35 U.S.C. 154(b) by 157 days.

(21) Appl. No.: 13/580,313

(22) PCT Filed: Feb. 21, 2011

(86) PCT No.: PCT/JP2011/053673
§ 371 (c)(1),
(2), (4) Date: Aug. 21, 2012

(87) PCT Pub. No.: WO2011/102510
PCT Pub. Date: Aug. 25, 2011

(65) Prior Publication Data
US 2012/0316362 A1    Dec. 13, 2012

(30) Foreign Application Priority Data

Feb. 22, 2010 (JP) .................................. 2010-035922

(51) Int. Cl.
*C07C 209/90* (2006.01)
*C07C 47/02* (2006.01)
*C07C 231/22* (2006.01)

(52) U.S. Cl.
CPC .................................. *C07C 231/22* (2013.01)
USPC .................................. 564/4; 564/2; 568/448

(58) Field of Classification Search
CPC .................................................. C07C 231/22
USPC .......................................... 564/4, 2; 568/448
See application file for complete search history.

(56) References Cited

U.S. PATENT DOCUMENTS

| 3,951,600 A | 4/1976 | Asano et al. |
| 4,343,899 A | 8/1982 | Watanabe et al. |
| 4,526,789 A * | 7/1985 | Clark et al. ............... 514/627 |
| 5,352,828 A | 10/1994 | Seki et al. |
| 2003/0088125 A1 | 5/2003 | Abe et al. |
| 2011/0006258 A1 | 1/2011 | Oda et al. |

FOREIGN PATENT DOCUMENTS

| EP | 2 006 390 A1 | 12/2008 | |
| EP | 2006390 | * 12/2008 | ............ C12P 13/02 |
| JP | 39-10109 B | 6/1964 | |
| JP | 40-7171 B | 4/1965 | |
| JP | 40-7172 B | 4/1965 | |
| JP | 41-1773 B | 2/1966 | |
| JP | 45-11284 B | 4/1970 | |
| JP | 48-62716 A | 9/1973 | |
| JP | 55-108290 A | 8/1980 | |
| JP | 6-92919 A | 4/1994 | |
| JP | 9-183760 A | 7/1997 | |
| JP | 2003-206268 A | 7/2003 | |
| WO | WO 2007/116781 A1 | 10/2007 | |
| WO | WO 2009/113617 A1 | 9/2009 | |

OTHER PUBLICATIONS

International Search Report, issued in PCT/JP2011/053673, dated May 24, 2011.

* cited by examiner

*Primary Examiner* — Paul A Zucker
*Assistant Examiner* — Mark Luderer
(74) *Attorney, Agent, or Firm* — Birch, Stewart, Kolasch & Birch, LLP

(57) ABSTRACT

The present invention provides a process for stabilizing an aqueous acrylamide solution. The present invention also provides a stable aqueous acrylamide solution containing acetaldehyde at a weight ratio relative to acrylamide of 1.5 mg/Kg to 4 mg/Kg.

4 Claims, No Drawings though polymerization inhibiting effect may adversely affect the polymerization operations during production of acrylamide polymers such as having difficulty to obtain desired high molecular weight polymers and reducing the polymerization speed, even when used in small amounts.

STABLE AQUEOUS ACRYLAMIDE SOLUTION

TECHNICAL FIELD

The present invention relates to a stable aqueous acrylamide solution. More specifically, the present invention relates to an aqueous acrylamide solution stabilized by suppressing polymerization of acrylamide, which is very easy to polymerize, without causing any adverse effect on its quality during its production and/or storage.

BACKGROUND ART

Acrylamide has many applications, such as flocculating agents, petroleum recovering agents, paper strength enhancers in the papermaking industry, and thickeners for papermaking, and is a useful substance as a raw material for polymers.

Among industrial processes for acrylamide production, formerly used is the sulfuric acid hydrolysis process which comprises the step of heating acrylonitrile together with sulfuric acid and water to obtain acrylamide sulfate salts. This process has then been replaced with the copper-catalyzed process in which acrylonitrile is hydrated in the presence of a copper catalyst (e.g., metal copper, reduced copper, Raney copper, etc.) to obtain acrylamide. In recent years, as a production process with fewer by-products, industrial production has also been conducted by the microbial process in which acrylamide is obtained by means of microbially-derived nitrile hydratase.

As in the case of many unsaturated monomers, acrylamide is easy to polymerize by the action of light or heat and also has the property of very easily polymerizing upon contact with the surface of iron, so that acrylamide has been difficult to stably handle while suppressing its polymerization during each step of its production and during its storage/keeping.

For this reason, various stabilizers have been proposed to stabilize acrylamide. Examples of these stabilizers include thiourea, ammonium rhodanide, nitrobenzol (Patent Document 1), ferron (Patent Document 2), furil dioxime (Patent Document 3), cyanide complex compound of chromium (Patent Document 4), p-nitrosodiphenylhydroxyamine (Patent Document 5) and so on.

PRIOR ART DOCUMENTS

Patent Documents

Patent Document 1: JP S39-10109 B (Kokoku Publication)
Patent Document 2: JP S40-7171 B (Kokoku Publication)
Patent Document 3: JP S40-7172 B (Kokoku Publication)
Patent Document 4: JP S41-1773 B (Kokoku Publication)
Patent Document 5: JP S45-11284 B (Kokoku Publication)

SUMMARY OF THE INVENTION

Problem to be Solved by the Invention

The stabilizers above are used to prevent polymerization during the steps of acrylamide production and/or to stabilize an aqueous acrylamide solution. However, they all correspond to polymerization inhibitors. Stabilizers with a smaller polymerization inhibiting effect have problems of reduced quality, e.g., discoloration and reduced purity of acrylamide, since they should be added in large amounts to acrylamide. On the other hand, stabilizers with a higher polymerization inhibiting effect may adversely affect the polymerization operations during production of acrylamide polymers such as having difficulty to obtain desired high molecular weight polymers and reducing the polymerization speed, even when used in small amounts.

Means to Solve the Problem

As a result of extensive and intensive efforts made to solve the problems stated above, the inventors of the present invention have found that when acrylamide is allowed to contain acetaldehyde, polymerization of acrylamide during its production and/or preservation can be suppressed without reducing the quality of acrylamide to thereby significantly improve its stability. This finding led to the completion of the present invention.

The stable aqueous acrylamide solution of the present invention is as follows.

The present invention is directed to an aqueous acrylamide solution, which contains acetaldehyde at a concentration of 1.5 mg/Kg to 4 mg/Kg of acrylamide.

Moreover, the stabilized aqueous acrylamide solution of the present invention may have an acrylamide concentration of 25% to 60%.

Further, the stabilized aqueous acrylamide solution of the present invention may use an aqueous acrylamide solution produced by hydration of acrylonitrile in the presence of a biocatalyst.

The present invention also provides a stabilizer for an aqueous acrylamide solution, which comprises acetaldehyde.

The present invention further provides a process for stabilizing an aqueous acrylamide solution, which comprises the step of adjusting acetaldehyde to a concentration of 1.5 mg/Kg to 4 mg/Kg of acrylamide.

Effect of the Invention

When acrylamide is allowed to contain acetaldehyde, polymerization of acrylamide can be suppressed without reducing the quality of acrylamide to thereby significantly improve its stability. Moreover, in the aqueous acrylamide solution of the present invention, the corrosive effect on the surface of iron is also suppressed to thereby achieve a more improved stabilizing effect.

Embodiments for Carrying Out the Invention

Hereinafter, embodiments of the present invention will be described. The following embodiments are examples provided for illustrating the present invention, and the present invention is not intended to be limited thereto. The present invention may be carried out in various embodiments without departing from the spirit of the invention.

The present specification incorporates the content of the specification of Japanese Patent Application No. 2010-035922 (filed on Feb. 22, 2010) based on which the present application claims priority. All publications cited herein, including technical literatures, patent laid-open publications, patent publications and other patent documents, are incorporated herein by reference in their entirety.

The aqueous acrylamide solution according to the present invention may be produced in any manner, e.g., by the sulfuric acid hydration process which is the process for earlier industrial production, by the copper-catalyzed process which is a current major process for industrial production, or by the microbial process which is recently industrialized, more preferably by the microbial process which allows production of high purity acrylamide with fewer reaction by-products. Examples of the microbial process for acrylamide production include the processes described in, for example, Japanese Patent No. 2548051, JP S56-17918 B (Kokoku Publication), JP S59-37951 B (Kokoku Publication), JP H2-470 A (Kokai Publication) and WO2009/113654.

A process for acrylamide production using a biocatalyst may be accomplished by continuous reaction (acrylamide is produced in a continuous manner) or by batch reaction (acrylamide is produced in a non-continuous manner). Preferred is, but not limited to, the process accomplished by continuous reaction.

As used herein, a process accomplished by continuous reaction is intended to mean a process wherein acrylamide is produced in a continuous manner without collecting the entire reaction mixture in the reactor while maintaining continuous or intermittent supply of raw materials for reaction (comprising a biocatalyst and acrylonitrile) and continuous or intermittent recovery of the reaction mixture (comprising the produced acrylamide).

The biocatalyst used to produce the aqueous acrylamide solution of the present invention includes animal cells, plant cells, cell organelles, microbial cells (living or dead microbial cells) or treated products thereof, which contain an enzyme catalyzing a desired reaction. Such treated products include a crude or purified enzyme extracted from the cells, as well as animal cells, plant cells, cell organelles, microbial cells (living or dead microbial cells) or enzyme molecules which are immobilized by entrapping, crosslinking or carrier binding techniques, etc.

Entrapping refers to a technique by which microbial cells or enzymes are enclosed within a fine lattice of polymer gel or coated with a semipermeable polymer membrane. Crosslinking refers to a technique by which enzymes are crosslinked with a reagent having two or more functional groups (i.e., a multifunctional crosslinking agent). Furthermore, carrier binding refers to a technique by which enzymes are bound to a water-insoluble carrier.

Examples of an immobilization carrier for use in immobilization include glass beads, silica gel, polyurethane, polyacrylamide, polyvinyl alcohol, carrageenan, alginic acid, agar and gelatin, etc.

Examples of the above microbial cells include microorganisms belonging to the genera *Nocardia, Corynebacterium, Bacillus, Pseudomonas, Micrococcus, Rhodococcus, Acinetobacter, Xanthobacter, Streptomyces, Rhizobium, Klebsiella, Enterobacter, Erwinia, Aeromonas, Citrobacter, Achromobacter, Agrobacterium* and *Pseudonocardia*, etc. More preferred microbial cells include *Rhodococcus rhodochrous* strain J1 (FERM BP-1478).

*Rhodococcus rhodochrous* strain J1 having nitrile hydratase activity was internationally deposited on Sep. 18, 1987 under Accession No. FERM BP-1478 with the International Patent Organism Depositary, the National Institute of Advanced Industrial Science and Technology (Chuo 6, 1-1-1 Higashi, Tsukuba, Ibaraki, Japan).

Information about the depositor is as follows.
Name: Hideaki Yamada
Address: 19-1 Kinomoto-cho, Matsugasaki, Sakyo-ku, Kyoto-shi, Kyoto Examples of an enzyme include nitrile hydratase produced by the above microorganisms.

Although the amount of the biocatalyst to be used will vary depending on the type and/or form of the biocatalyst, it is preferably adjusted such that the activity of the biocatalyst to be introduced into a reactor is around 50 to 200 U per mg of dried microbial cells at a reaction temperature of 10° C. The above unit "U (unit)" is intended to mean that one micromole of acrylamide is produced for one minute from acrylonitrile, which is measured by using acrylonitrile to be used for production.

Although the acrylonitrile concentration during reaction will vary depending on the type and/or form of the biocatalyst, it is preferably around 0.5% to 15.0% by weight.

When the production process of the present invention is accomplished by continuous reaction, the flow rate upon collection of the reaction mixture from the reactor may be determined in line with the introduction rate of acrylonitrile and the biocatalyst so as to ensure continuous production without collecting the entire reaction mixture in the reactor.

Acrylamide thus produced is preferably used in the form of a 25% to 60% by weight aqueous solution. If the acrylamide concentration is lower than 25% by weight, it is economically disadvantageous from the industrial standpoint because the tank volume used for storage or keeping will be excessively large and transport costs will also be increased. Likewise, if the concentration is higher than 60% by weight, crystals of acrylamide will precipitate near ambient temperature and hence a heating system is required, so that not only facility costs will be increased, but also temperature control and other operations will be complicated. For these reasons, the upper limit for the concentration of the aqueous acrylamide solution of the present invention may be set to, for example, 60% by weight, more preferably 55% by weight, and most preferably 50% by weight, as long as it is within the range where crystals of acrylamide will not precipitate even near ambient temperature. The lower limit for the concentration of the aqueous acrylamide solution of the present invention may be set to, for example, 25% by weight, more preferably 35% by weight, and most preferably 40% by weight.

The stable aqueous acrylamide solution in the present invention preferably contains acetaldehyde at a weight ratio relative to acrylamide of 1.5 mg/Kg to 4 mg/Kg, more preferably 2 to 3 mg/Kg. At a content lower than 1.5 mg/Kg, acetaldehyde produces little stabilizing effect to suppress polymerization of acrylamide. At a content higher than 4 mg/Kg, the stabilizing effect will also become smaller.

For the purpose of facilitating stabilization, the aqueous acrylamide solution according to the present invention may further comprise, in addition to acetaldehyde, at least one water-soluble monocarboxylic acid salt containing two or more carbon atoms, which is added as an acid at a weight ratio relative to acrylamide of 20 to 5000 mg/Kg.

Such a monocarboxylic acid salt may be a salt of either a saturated monocarboxylic acid or an unsaturated monocarboxylic acid, as specifically exemplified by acetic acid, propionic acid, n-caproic acid and so on for saturated carboxylic acids, as well as acrylic acid, methacrylic acid, vinylacetic acid and so on for unsaturated carboxylic acids. Typical salts are sodium salts, potassium salts, and ammonium salts.

Acetaldehyde is generally found in a trace amount as an impurity in acrylonitrile, which is a raw material for acrylamide. When acrylonitrile with low acetaldehyde content is used for acrylamide production to thereby obtain an aqueous acrylamide solution whose acetaldehyde content is lower than 1.5 mg/Kg of acrylamide, acetaldehyde may be added to give a desired concentration.

For addition of acetaldehyde to acrylamide, it may be added to acrylonitrile, which is a raw material for acrylamide, or water (raw material) or a catalyst, or may be added during any step of acrylamide production, or may be added to the produced acrylamide. Preferred is addition to the produced acrylamide in which the acetaldehyde concentration is more easily adjusted.

Acetaldehyde used may be a commercially available product or a product synthesized by techniques known in the art. If a very small amount of acetaldehyde is added to the aqueous acrylamide solution, acetaldehyde may be diluted for easy addition and added. In this case, water may be used for dilution. However, if it is not desired that the acrylamide concentration is reduced by addition of such a diluted acetaldehyde solution, acetaldehyde may be diluted with an aqueous acrylamide solution having a desired concentration, and this diluted solution may be added to the aqueous acrylamide solution.

On the other hand, when the acetaldehyde content in acrylonitrile is high enough to give an aqueous acrylamide solution containing acetaldehyde at a concentration greater than 4 mg/Kg of acrylamide, such acrylonitrile may be purified to remove acetaldehyde, thereby obtaining the aqueous acrylamide solution of the present invention.

In cases where acetaldehyde is removed or added, the acetaldehyde content in the aqueous acrylamide solution may be measured by gas chromatography mass spectrometry, liquid chromatography mass spectrometry, MBTH method (3-methyl-2-benzothiazolinone hydrazone method) or the like to determine whether it is within a prescribed concentration range.

For removal of acetaldehyde contained in acrylonitrile, acrylonitrile may be contacted with an ion exchange resin. Techniques for removing aldehyde compounds contained in acrylonitrile by means of an ion exchange resin can be found, e.g., in JP H7-145123 A (Kokai Publication) and JP 2000-16978 A (Kokai Publication), etc.

During production of acrylamide polymers, the stabilized aqueous acrylamide solution of the present invention has almost no effect on polymerization within the above range of acetaldehyde content. Therefore, depending on the subsequent purpose, the stabilized aqueous acrylamide solution of the present invention can be subject to the polymerization step in a state containing acetaldehyde to obtain a desired acrylamide polymer.

In another embodiment, the present invention provides a stabilizer for an aqueous acrylamide solution, which comprises acetaldehyde. The stabilizer of the present invention may be added in any amount relative to acrylamide. The amount may be increased or decreased as appropriate with no limitation, but preferably set to an amount which achieves a desired acetaldehyde concentration in the aqueous acrylamide solution supplemented with this stabilizer (e.g., 1.5 mg/Kg to 4 mg/Kg, preferably 2 mg/Kg to 3 mg/Kg, as a weight ratio relative to acrylamide). The stabilizer of the present invention may further comprise other components in addition to acetaldehyde, as long as the stabilizing effect of acetaldehyde is not reduced. Although the stabilizer of the present invention exerts a sufficient effect when used alone, it may be used in admixture with other known stabilizers.

In yet another embodiment, the present invention provides a process for stabilizing an aqueous acrylamide solution, which comprises the step of adjusting acetaldehyde to a concentration of 1.5 mg/Kg to 4 mg/Kg of the aqueous acrylamide solution. The acetaldehyde concentration may be adjusted by, but not limited to, addition or removal of acetaldehyde. In this process, addition of acetaldehyde to acrylamide may be accomplished by addition to acrylonitrile, which is a raw material for acrylamide, or water (raw material) or a catalyst, by addition during any step of acrylamide production, or by addition to the produced acrylamide. Acetaldehyde is preferably added to the produced acrylamide in which the acetaldehyde concentration is more easily adjusted. On the other hand, for removal of acetaldehyde, acrylonitrile, which is a raw material for acrylamide, may be purified, or alternatively, the produced acrylamide may be purified. Acetaldehyde is preferably removed from the raw material acrylonitrile which is easier to purify. Further, adjustment of the acetaldehyde concentration may be accomplished by diluting an aqueous acrylamide solution which contains acetaldehyde at a certain concentration (e.g., greater than 4 mg/Kg) to give a desired acetaldehyde concentration. Examples of a solution for use in dilution include an aqueous acrylamide solution, as well as an aqueous solution of a monocarboxylic acid salt, etc.

EXAMPLES

The present invention will be further described in more detail by way of the following examples, which are not intended to limit the scope of the present invention.

Example 1

(Aqueous Acrylamide Solution Containing 1.5 mg/Kg Acetaldehyde)

A commercially available 50% aqueous acrylamide solution (a product of Dia-Nitrix Co., Ltd.; produced by hydration of acrylonitrile according to the microbial process, pH 6.8, containing 200 mg/Kg acrylic acid (relative to acrylamide)) was analyzed for its acetaldehyde concentration by liquid chromatography (HPLC).

More specifically, an aqueous acrylamide solution was produced from acrylonitrile according to the procedures described in Example 2 of Japanese Patent No. 2548051. Then, the resulting aqueous acrylamide solution was taken in a volume of 1 ml into a test tube, followed by addition of a saturated 2,4-DNPH solution (50 μl) containing excess 2,4-dinitrophenylhydrazine (2,4-DNPH) in acetonitrile. After the test tube was shaken, concentrated hydrochloric acid (10 μl) was added and the test tube was soaked in a thermostatic bath equipped with a shaker, followed by shaking at 50° C. for 20 minutes. After 20 minutes, the solution in the test tube was injected in a volume of 20 μl into HPLC to measure its acetaldehyde concentration. HPLC analysis was conducted under the following conditions.

TABLE 1

| | |
|---|---|
| Column | Inertsil ODS-80A (GL Sciences Inc.) |
| Eluent | Acetonitrile:tetrahydrofuran:water = 25:15:60 |
| Injection volume | 20 μl |
| Flow rate | 1.5 ml/min |
| Detection conditions | UV 374 nm |
| Oven temperature | 50° C. |
| Pressure | 91 kgf/cm$^2$ |

As a result, the acetaldehyde concentration was 1.1 mg/Kg (relative to acrylamide).

Acetaldehyde (Kanto Chemical Co., Inc., Cica reagent grade (Cica-Tokkyu)) was diluted with pure water to prepare a 100 mg/Kg aqueous acetaldehyde solution, 0.6 g of which was then added to the commercially available 50% aqueous acrylamide solution (300 g) to give an acetaldehyde concentration of 1.5 mg/Kg of acrylamide.

The 50% aqueous acrylamide solution containing 1.5 mg/Kg acetaldehyde was taken in an amount of 30 g and introduced into a 50 ml polypropylene container (a product of AS ONE Corporation, under the trade name Ai-Boy wide-mouth bottle).

A toroidal iron chip (a product of Misumi Corporation; Model No. WSS6, inner diameter: 6 mm, outer diameter: 13 mm) was washed with acetone and then with pure water, followed by drying. After drying, this iron chip was introduced into the 50 ml polypropylene container containing the aqueous acrylamide solution supplemented with acetaldehyde.

This polypropylene container was held in a thermostat kept at 70° C. to measure the number of days required until the aqueous acrylamide solution was polymerized.

After 40 days, a popcorn-like polymerized product was generated. The iron chip showed no rust.

Example 2

(Aqueous Acrylamide Solution Containing 4 mg/Kg Acetaldehyde)

The same procedure as shown in Example 1 was repeated to measure the number of days required until an aqueous acrylamide solution was polymerized, except that the commercially available 50% aqueous acrylamide solution (300 g) was supplemented with 0.435 g of a 1000 mg/Kg aqueous acetaldehyde solution diluted with pure water to give an acetaldehyde concentration of 4 mg/Kg of acrylamide.

After 44 days, a popcorn-like polymerized product was generated. The iron chip showed no rust.

Comparative Example 1

(Aqueous Acrylamide Solution Containing 1.1 mg/Kg Acetaldehyde)

The same procedure as shown in Example 1 was repeated to measure the number of days required until an aqueous acrylamide solution was polymerized, except that the commercially available 50% aqueous acrylamide solution was used.

After 3 days, a popcorn-like polymerized product was generated. The iron chip was rusted.

Comparative Example 2

(Aqueous Acrylamide Solution Containing 5 mg/Kg Acetaldehyde)

The same procedure as shown in Example 1 was repeated to measure the number of days required until an aqueous acrylamide solution was polymerized, except that the commercially available 50% aqueous acrylamide solution (300 g) was supplemented with 0.585 g of a 1000 mg/Kg aqueous acetaldehyde solution diluted with pure water to give an acetaldehyde concentration of 5.0 mg/Kg of acrylamide.

After 7 days, a popcorn-like polymerized product was generated. The iron chip was rusted.

As is evident from the above results, aqueous acrylamide solutions containing acetaldehyde at a concentration of 1.5 mg/Kg to 4 mg/Kg (relative to acrylamide) are maintained extremely stable due to a high suppressive effect on polymerization, simultaneously with suppressing the formation of rust on iron chips.

TABLE 2

|  | Acetaldehyde concentration [mg/Kg] (relative to acrylamide) | Days required until polymerization [days] | Rust on iron chip |
| --- | --- | --- | --- |
| Example 1 | 1.5 | 40 | Not observed |
| Example 2 | 4.0 | 44 | Not observed |
| Comparative Example 1 | 1.1 | 3 | Observed |
| Comparative Example 2 | 5.0 | 7 | Observed |

Industrial Applicability

According to the present invention, an aqueous acrylamide solution can be stabilized in a simple manner. Therefore, the present invention is useful as a process for preventing polymerization of acrylamide during production, storage and/or transport of an aqueous acrylamide solution.

The invention claimed is:

1. An aqueous acrylamide solution, which contains acetaldehyde to acrylamide at a concentration of 1.5 mg acetaldehyde/Kg acrylamide to 4 mg acetaldehyde/Kg acrylamide.

2. The aqueous acrylamide solution according to claim 1, wherein the acrylamide concentration is 25% to 60% by weight aqueous solution.

3. The aqueous acrylamide solution according to claim 1 or 2, wherein the acrylamide is produced by hydration of acrylonitrile in the presence of a biocatalyst.

4. A process for stabilizing an aqueous acrylamide solution, which comprises the step of adjusting the concentration of acetaldehyde to 1.5 mg acetaldehyde/Kg acrylamide to 4 mg acetaldehyde/Kg acrylamide.

* * * * *